United States Patent [19]

Toyama et al.

[11] 4,036,630
[45] July 19, 1977

[54] SYNERGISTIC HERBICIDAL COMPOSITION FOR PADDY FIELDS

[75] Inventors: Teruhiko Toyama, Fujisawa; Yoshio Takasawa, Chigasaki, both of Japan

[73] Assignee: Mitsui Toatsu Chemicals, Incorporated, Tokyo, Japan

[21] Appl. No.: 677,534

[22] Filed: Apr. 16, 1976

Related U.S. Application Data

[62] Division of Ser. No. 290,002, Sept. 18, 1972, Pat. No. 4,001,004.

[51] Int. Cl.² ............................................. A01N 9/12
[52] U.S. Cl. .................................... 71/88; 71/118
[58] Field of Search .................................. 71/88, 118

[56] References Cited

U.S. PATENT DOCUMENTS

| | | | |
|---|---|---|---|
| 3,573,031 | 3/1971 | Tilles | 71/100 |
| 3,582,314 | 6/1971 | Konnai et al. | 71/88 |
| 3,718,455 | 2/1973 | Baker et al. | 71/118 |
| 3,767,623 | 10/1973 | Alt | 71/118 |

FOREIGN PATENT DOCUMENTS

| | | | |
|---|---|---|---|
| 46-14077 | 4/1971 | Japan | 71/118 |

*Primary Examiner*—Glennon H. Hollrah
*Attorney, Agent, or Firm*—Fisher, Christen & Sabol

[57] ABSTRACT

A synergistic herbicidal composition for use in paddy fields comprising a mixture of α-(β-naphthoxy)-propionanilide and a thiocarbamate compound.

6 Claims, No Drawings

SYNERGISTIC HERBICIDAL COMPOSITION FOR PADDY FIELDS

This is a division, of application Ser. No. 290,002, filed Sept. 18, 1972, now U.S. Pat. No. 4,001,004.

BACKGROUND OF THE INVENTION

1. Field of the Invention

This invention relates to a novel herbicidal composition for use in paddy fields.

2. Description of the Prior Art

Among existing herbicides used in transplanted paddy fields, pentachlorophenol, diphenyl ethers, etc. are well known for their excellent herbicidal effects when applied at the initial stage of growth of weeds. On the other hand, DCPA and SWEP.M (a mixture containing 20% of methyl-N-(3,4-dichlorophenyl) carbamate and 0.7% of ethyl 2-methyl-4-chlorophenoxy acetate) are also used as a herbicide but they are applied after the weeds have grown to some extent. DCPA, however, requires drainage of water completely from the paddy fields before its application. If the draining is insufficient, DCPA fails to give satisfactory weeding effects. In this connection, it is practically extremely difficult to drain water completely from paddy fields, so that DCPA is rarely employed in practical application. SWEP.M may be used in fields filled with water, but its herbicidal effects and phytotoxicity on rice plants vary considerably depending on particular temperatures and soil conditions, i.e., the herbicidal activities of the agent are reduced under low temperature conditions while the adverse effects of the agent become pronounced under high temperature conditions. Furthermore, in the paddy field with continued leaching of water, the agent penetrates into the soil and is absorbed by roots of the rice plants, causing damage to the rice plants.

In addition, when SWEP.M is used in combination with carbamate or organic phosphorous base insecticides, a great problem occurs in practical applications in that rice plants are seriously damaged. Accordingly, it is strongly desired to develop a novel herbicide which has stable effects in removing weeds which have grown to a certain degree, without resulting in phytotoxicity to the rice plants.

SUMMARY OF THE INVENTION

It is therefore an object of the invention to provide a novel herbicidal composition of the nature described which will overcome the above-described disadvantages.

It is another object of the invention to provide a herbicidal composition which is effective for controlling annual weeds or perennial weeds which have already grown to a certain degree.

It is still another object of the invention to provide a herbicidal composition which retains its herbicidal effects for a long period of time.

It is yet another object of the invention to provide a herbicidal composition which may be used without draining of water in the paddy fields.

An important feature of the invention resides in a herbicidal composition for use in paddy fields comprising α-(β-naphthoxy)-propionanilide and a thiocarbamate compound expressed by the formula

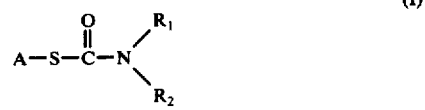

(I)

Wherein A represents $C_2H_5$, $CH(CH_3)_2$,

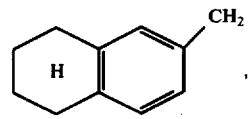

or

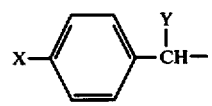

wherein X represents Cl, F, $CH_3$, $C_2H_5$, n-$C_3H_7$, iso-$C_3H_7$, tert-$C_4H_9$, $OCH_3$ or $SCH_3$, and Y represents H or $CH_3$); $R_1$ and $R_2$ represent alkyl containing 1 to 3 carbon atoms or $R_1$ and $R_2$, together with N form a 6-membered heterocyclic ring (1-hexamethyleneimine).

DESCRIPTION OF THE PREFERRED EMBODIMENT

The α-(β-naphthoxy)-propionanilide (hereinafter referred to as NOPA for abbreviation) has a melting point from 125° to 127° C.

The present inventors discovered as a result of an extensive study on various kinds of herbicides that the above-described herbicidal composition has remarkably high effects for controlling particularly annual weeds and perennial weeds at a relatively advanced stage of growth and retains herbicidal activities for a long period of time, so that it is made possible to control weeds completely which would germinate after the treatment.

The composition of the present invention includes NOPA which is effective for controlling annual and perennial broad-leaved weeds and the thiocarbamate compound (I) which is effective for controlling narrow-leaved weeds, with the result that excellent synergistic effects of these two compounds are obtained. Moreover, the composition does not necessarily require drainage of the paddy fields and gives excellent effects even when used in a water-filled field. The mixing ratio of NOPA to the compound (I) is preferably 1 : 1–4 but it may be varied over a relatively wide range according to particular requirements.

The compound (I) of the herbicidal composition of the present invention includes the following:

Compound A

Compound B

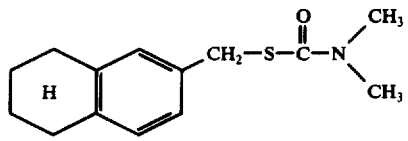

(boiling point 170-173° C/0.5mmHg)

Compound C

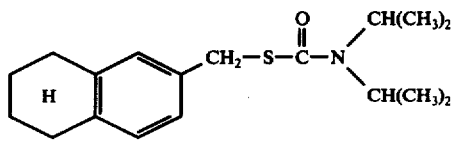

(boiling point 214-215° C/2mmHg)

Compound E

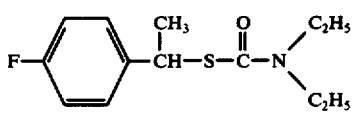

(boiling point 128.5-130.5/0.4mmHg)

Compound G

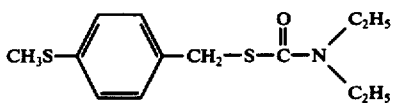

(boiling point 150-157° C/0.03-0.025mmHg)

Compound I

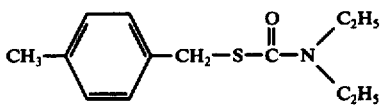

(boiling point 142-145° C/0.2mmHg)

Compound K

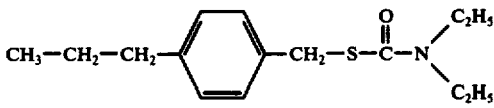

(boiling point 189-190° C/10mmHg)

Compound M

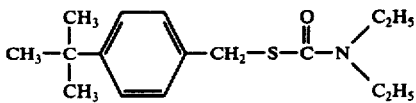

(boiling point 160-165° C/0.3mmHg)

Compound O

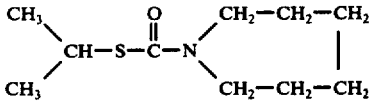

(n$_D^{21}$1.5080)

-continued

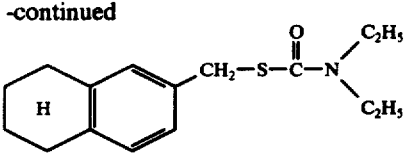

(boiling point 212-217° C/2mmHg)

Compound D

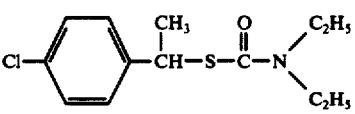

(boiling point 140-147 ° C/0.45mmHg)

Compound F

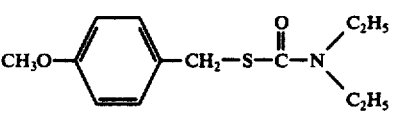

(boiling point 133-131° C/0.06-0.05mmHg)

Compound H

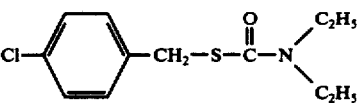

(boiling point 163-167° C/4mmHg)

Compound J

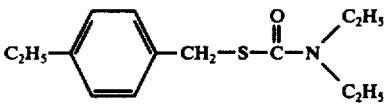

(boiling point 167-168° C/4mmHg)

Compound L

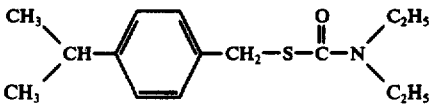

(boiling point 150-152° C/0.3mmHg)

Compound N

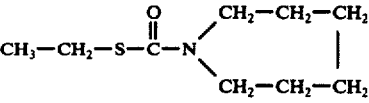

(boiling point 136.5-137° C.10mmHg)

The herbicidal composition of the present invention may be used in combination with solid carriers such as diluent, filler and the like. If necessary, the herbicidal composition may be used in the form of a wettable powder or granules by addition of adjuvants such as a stabilizing agent, a dispersing agent, a suspending agent, a spreader, a penetrating agent, a wetting agent and the like. Moreover, the herbicide of the present invention may be provided in a form mixed with agricultural chemicals such as fungicides, insecticides or other herbicides, or fertilizers such as urea, ammonium sulfate, ammonium phosphate, potassium salts or soil conditioners and the like. When the herbicide of the present invention is formed into granules, it is desired that such granules contain therein 1 - 20% by weight of the composition of the present invention, and when formed into a wettable powder, 10 - 50%.

The herbicidal activities of the composition of the present invention will be understood from the following Experimental Examples.

EXPERIMENTAL EXAMPLE 1

3.3 Kg of soil having a variety of weeds naturally grown in paddy fields were put into a/5000 wagner pots. 0.8g. of each of $N, P_2O_5$ and $K_2O$ provided in the form of fertilizer was placed in the soil to which was then added a suitable amount of water. The mixture was fully agitated and the wagner pots were brought to irrigated conditions. On the other hand, rice plant seedlings (3 leaf stage) were grown in a greenhouse, and two stubbles of rice plants, each having two seedlings, were planted in each pot at a depth of 3cm. Then, 200mg. of barnyard grass seeds were sown over and mixed with the surface soil of each of the pots which were placed in a greenhouse to grow the seeds. 15 days after the planting, there grew in the pots weeds such as barnyard grass of leaf age 2.5 (5–10cm), *Cyperus difformis* (3–5cm), *Monochoria vaginalis* (2–5cm), *Rotala indica* (2–5cm) and *Dopatrium junceum* (2–5cm). A predetermined amount of NOPA, or a granulate of the compound (1) or a mixture of both compounds was added, as shown in Table I, to the water of each pot. One month after the treatment, the remaining amount of the weeds was examined with the results as shown in Table 1. During the test, the water depth of the pot was maintained at 3cm.

Table

| Dose of Composition Applied (A.I g/a) | | Rice Plant (% to hand-weeding weight) | | Weeds (% to no weeding weight) | | | | | |
|---|---|---|---|---|---|---|---|---|---|
| | | Number of tiller | Weight | Barn-yard grass | Cyperus difformis | Monochoria vaginalis | Rotala indica | Callitriche verna | Eleocharis acicularis |
| NOPA | 2 | 100.0 | 103.2 | 100.0 | 100.0 | 16.3 | 11.4 | 31.4 | 38.2 |
| | 5 | 100.0 | 101.6 | 100.0 | 92.1 | 4.1 | 3.2 | 18.6 | 12.3 |
| | 10 | 100.0 | 100.1 | 99.8 | 84.6 | 0.0 | 0.0 | 0.0 | 0.0 |
| | 20 | 100.0 | 99.4 | 94.3 | 71.4 | 0.0 | 0.0 | 0.0 | 0.0 |
| Compound B | 5 | 100.0 | 101.3 | 28.3 | 18.3 | 94.2 | 88.1 | 98.2 | 26.8 |
| | 10 | 100.0 | 99.1 | 14.2 | 0.0 | 87.1 | 71.9 | 78.3 | 16.1 |
| | 20 | 100.0 | 97.4 | 0.0 | 0.0 | 53.4 | 37.4 | 54.9 | 10.0 |
| Compound D | 5 | 100.0 | 99.8 | 25.3 | 14.9 | 89.3 | 80.5 | 96.3 | 21.6 |
| | 10 | 100.0 | 98.3 | 5.4 | 0.0 | 72.8 | 68.4 | 69.2 | 13.5 |
| | 20 | 90.0 | 91.2 | 0.0 | 0.0 | 42.3 | 31.1 | 54.6 | 0.0 |
| Compound E | 5 | 100.0 | 93.5 | 37.9 | 31.2 | 100.0 | 96.8 | 100.0 | 63.2 |
| | 10 | 90.0 | 89.2 | 19.6 | 11.3 | 91.3 | 83.8 | 84.6 | 39.8 |
| | 20 | 80.0 | 86.4 | 8.7 | 0.0 | 83.4 | 71.2 | 68.1 | 16.5 |
| Compound F | 5 | 100.0 | 100.0 | 47.8 | 38.1 | 88.1 | 90.0 | 92.4 | 88.4 |
| | 10 | 100.0 | 98.2 | 18.4 | 14.2 | 80.0 | 82.1 | 78.9 | 70.0 |
| | 20 | 90.0 | 95.6 | 0.0 | 0.0 | 68.4 | 72.0 | 66.4 | 43.9 |
| Compound G | 5 | 100.0 | 99.1 | 49.3 | 48.1 | 90.0 | 89.9 | 93.4 | 70.4 |
| | 10 | 100.0 | 98.6 | 13.4 | 24.1 | 82.1 | 88.7 | 91.2 | 68.2 |
| | 20 | 90.0 | 94.5 | 0.0 | 0.0 | 64.1 | 69.3 | 80.4 | 54.1 |
| Compound H | 5 | 100.0 | 101.4 | 20.4 | 10.3 | 82.1 | 30.1 | 40.0 | 38.9 |
| | 10 | 110.0 | 99.8 | 0.0 | 0.0 | 20.0 | 0.8 | 30.0 | 24.1 |
| | 20 | 110.0 | 92.4 | 0.0 | 0.0 | 0.0 | 0.0 | 10.0 | 0.0 |
| Compound J | 5 | 104.2 | 101.6 | 18.4 | 12.4 | 79.4 | 31.4 | 41.0 | 36.5 |
| | 10 | 100.1 | 100.7 | 0.0 | 0.0 | 21.0 | 0.9 | 28.6 | 21.4 |
| | 20 | 102.4 | 99.8 | 0.0 | 0.0 | 0.0 | 0.0 | 10.1 | 0.0 |
| Compound K | 5 | 107.6 | 102.7 | 16.2 | 10.4 | 62.7 | 32.1 | 32.6 | 30.6 |
| | 10 | 109.2 | 101.6 | 0.0 | 0.0 | 19.1 | 0.9 | 21.4 | 19.8 |
| | 20 | 101.4 | 100.2 | 0.0 | 0.0 | 0.0 | 0.0 | 9.7 | 0.0 |
| Compound N | 5 | 105.6 | 100.7 | 21.9 | 10.9 | 81.2 | 45.0 | 25.0 | 30.2 |
| | 10 | 104.3 | 100.2 | 0.0 | 0.0 | 21.9 | 29.6 | 20.1 | 18.1 |
| | 20 | 100.7 | 100.6 | 0.0 | 0.0 | 1.8 | 10.8 | 10.7 | 1.9 |
| NOPA + Compound B | | | | | | | | | |
| 5 | 10 | 110.0 | 104.2 | 6.0 | 4.8 | 7.9 | 0.8 | 7.1 | 8.8 |
| 5 | 20 | 100.0 | 101.2 | 0.0 | 0.0 | 0.0 | 0.0 | 6.0 | 7.0 |
| 10 | 10 | 100.0 | 99.8 | 1.0 | 0.8 | 0.0 | 0.8 | 5.8 | 5.0 |
| 10 | 20 | 100.0 | 97.4 | 0.0 | 0.0 | 0.0 | 0.0 | 0.0 | 0.0 |
| NOPA + Compound D | | | | | | | | | |
| 5 | 10 | 110.0 | 98.2 | 4.4 | 2.3 | 8.9 | 2.4 | 10.0 | 4.2 |
| 5 | 20 | 110.0 | 98.8 | 0.0 | 0.0 | 0.0 | 0.0 | 5.2 | 0.0 |
| 10 | 10 | 100.0 | 99.7 | 0.8 | 1.2 | 0.0 | 0.0 | 4.3 | 0.0 |
| 10 | 20 | 90.0 | 99.4 | 0.0 | 0.0 | 0.0 | 0.0 | 0.0 | 0.0 |
| NOPA + Compound E | | | | | | | | | |
| 10 | 10 | 90.0 | 103.1 | 0.9 | 12.2 | 10.0 | 10.0 | 14.8 | 30.0 |
| 20 | 20 | 100.0 | 99.8 | 0.0 | 0.0 | 0.0 | 0.0 | 0.0 | 0.0 |
| NOPA + Compound G | | | | | | | | | |
| 10 | 20 | 100.0 | 107.4 | 0.0 | 12.2 | 10.0 | 10.0 | 12.4 | 5.0 |
| 20 | 20 | 110.0 | 99.8 | 0.0 | 0.0 | 0.0 | 0.0 | 0.0 | 0.0 |
| NOPA + Compound H | | | | | | | | | |
| 5 | 10 | 100.0 | 107.4 | 6.0 | 0.8 | 5.4 | 10.0 | 10.4 | 5.0 |
| 5 | 20 | 100.0 | 103.1 | 0.0 | 0.0 | 0.0 | 0.0 | 0.4 | 0.0 |
| 10 | 10 | 100.0 | 99.8 | 0.0 | 0.0 | 0.0 | 0.0 | 8.4 | 0.0 |
| 10 | 20 | 100.0 | 97.9 | 0.0 | 0.0 | 0.0 | 0.0 | 0.0 | 0.0 |
| 20 | 20 | 100.0 | 98.8 | 0.0 | 0.0 | 0.0 | 0.0 | 10.0 | 0.0 |
| NOPA + Compound J | | | | | | | | | |
| 5 | 5 | 100.1 | 108.4 | 2.7 | 0.2 | 2.1 | 4.8 | 6.7 | 1.7 |
| 5 | 10 | 100.0 | 100.6 | 0.0 | 0.0 | 0.0 | 0.0 | 0.0 | 0.0 |
| 10 | 10 | 100.7 | 100.3 | 0.0 | 0.0 | 0.0 | 0.0 | 0.0 | 0.0 |
| 20 | 20 | 100.4 | 100.1 | 0.0 | 0.0 | 0.0 | 0.0 | 0.0 | 0.0 |
| NOPA + Compound K | | | | | | | | | |
| 5 | 10 | 100.4 | 100.6 | 4.7 | 0.6 | 2.9 | 6.8 | 6.5 | 3.9 |
| 10 | 5 | 100.7 | 100.5 | 0.0 | 0.0 | 0.0 | 0.0 | 0.0 | 0.0 |

Table -continued

| Dose of Composition Applied (A.I g/a) | | Rice Plant (% to hand-weeding weight) | | Weeds (% to no weeding weight) | | | | | |
|---|---|---|---|---|---|---|---|---|---|
| | | Number of tiller | Weight | Barn-yard grass | Cyperus difformis | Monochoria vaginalis | Rotala indica | Callitriche verna | Eleocharis acicularis |
| 10 | 10 | 100.6 | 100.1 | 0.0 | 0.0 | 0.0 | 0.0 | 0.0 | 0.0 |
| 10 | 20 | 100.4 | 100.0 | 0.0 | 0.0 | 0.0 | 0.0 | 0.0 | 0.0 |
| NOPA+Compound N | | | | | | | | | |
| 5 | 5 | 100.7 | 100.2 | 3.1 | 0.9 | 2.8 | 7.2 | 8.7 | 4.2 |
| 10 | 10 | 100.6 | 100.1 | 0.0 | 0.0 | 0.0 | 0.0 | 0.0 | 0.0 |
| 10 | 20 | 100.6 | 100.1 | 0.0 | 0.0 | 0.0 | 0.0 | 0.0 | 0.0 |
| MCPA* | 2 | 70.0 | 80.9 | 40.8 | 24.4 | 5.0 | 10.0 | 10.0 | 15.0 |
| | 4 | 60.0 | 71.2 | 12.8 | 12.2 | 0.0 | 0.0 | 0.0 | 0.0 |
| | 6 | 40.0 | 67.1 | 2.3 | 10.0 | 0.0 | 0.0 | 0.0 | 0.0 |
| NIP** | 20 | 100.0 | 98.8 | 60.0 | 40.0 | 80.0 | 60.0 | 74.0 | 79.9 |
| no weeding | | 90.0 | 92.1 | 100 (2.64g /pot) | 100 (0.22 /pot) | 100 (0.24 /pot) | 100 (0.10 /pot) | 100 (0.07 /pot) | 100 (0.09 /pot) |
| hand weeding | | 100 (10 tillers) | 100 3.45g /pot | | | | | | |

Note)
*Sodium 2-methyl-4-chlorophenoxy acetate
**2,4-dichloro-4'-nitrodiphenyl ether

EXPERIMENTAL EXAMPLE 2

In a concrete pot having a dimension of 50 × 50 × 50 cm was put soil of paddy fields having a variety of weeds naturally grown in the paddy fields. Rice plants were grown in the pot to use them as test specimens. The rice plants were transplanted in stubbles each containing two seedlings and spaced at a distance of 20 cm from each other. 15 days after transplanting a predetermined amount of the compounds to be tested was sprayed over the pot. One month after the treatment with the compounds, the remaining amount of weeds was examined with the test results as shown in Table 2. During the test the water depth of the concrete pot was maintained at 3 cm.

Table 2

| Dose of Composition Applied (A.I g/a) | | Rice Plant (% to hand weeding weight) | | Weeds (% to no weeding weight) | | | |
|---|---|---|---|---|---|---|---|
| | | Number of tiller | Weight | Barn-yard grass | Eleocharis acicularis | Others Broad-leaved weeds | Narrow-leaved weeds |
| NOPA | 5 | 104.0 | 101.8 | 99.8 | 10.0 | 21.8 | 80.0 |
| | 10 | 100.0 | 100.9 | 80.7 | 0.0 | 0.0 | 10.0 |
| | 20 | 100.0 | 102.1 | 80.4 | 0.0 | 0.0 | 0.0 |
| NOPA+Compound A | | | | | | | |
| 20 | 20 | 104.0 | 106.4 | 10.0 | 2.8 | 0.0 | 0.0 |
| NOPA+Compound B | | | | | | | |
| 10 | 10 | 96.0 | 103.4 | 0.0 | 0.0 | 0.0 | 0.0 |
| 20 | 20 | 100.0 | 107.7 | 0.0 | 0.0 | 0.0 | 0.0 |
| NOPA+Compound C | | | | | | | |
| 20 | 20 | 96.0 | 104.3 | 0.9 | 5.4 | 0.0 | 0.0 |
| NOPA+Compound D | | | | | | | |
| 10 | 20 | 104.0 | 101.4 | 0.0 | 0.0 | 0.0 | 0.0 |
| 20 | 20 | 104.0 | 102.8 | 0.0 | 0.0 | 0.0 | 0.0 |
| NOPA+Compound E | | | | | | | |
| 20 | 20 | 100.0 | 101.4 | 9.8 | 2.3 | 0.0 | 0.0 |
| NOPA+Compound F | | | | | | | |
| 20 | 20 | 104.0 | 99.0 | 0.0 | 0.0 | 0.0 | 0.0 |
| NOPA+Compound G | | | | | | | |
| 20 | 20 | 108.0 | 98.8 | 0.0 | 0.0 | 0.0 | 0.0 |
| NOPA+Compound H | | | | | | | |
| 5 | 10 | 104.0 | 109.4 | 8.0 | 0.2 | 0.7 | 0.4 |
| 5 | 20 | 104.0 | 100.8 | 0.0 | 0.0 | 0.0 | 0.0 |
| 10 | 10 | 108.0 | 100.4 | 4.0 | 0.1 | 0.0 | 0.0 |
| 10 | 20 | 100.0 | 102.1 | 0.0 | 0.0 | 0.0 | 0.0 |
| 20 | 20 | 104.0 | 97.7 | 0.0 | 0.0 | 0.0 | 0.0 |
| NOPA+Compound I | | | | | | | |
| 20 | 20 | 101.0 | 108.4 | 0.2 | 0.1 | 0.0 | 0.0 |
| NOPA+Compound J | | | | | | | |
| 10 | 10 | 104.2 | 100.8 | 0.0 | 0.0 | 0.0 | 0.0 |
| NOPA+Compound L | | 99. | | | | | |
| 10 | 10 | 99.4 | 98.7 | 0.0 | 0.0 | 0.0 | 0.0 |
| NOPA+Compound M | | | | | | | |
| 10 | 10 | 107.3 | 100.9 | 0.0 | 0.0 | 0.0 | 0.0 |
| NOPA+Compound N | | | | | | | |
| 10 | 10 | 104.0 | 102.4 | 0.0 | 0.0 | 0.0 | 0.0 |
| MCPA | 3 | 96.0 | 92.4 | 76.1 | 10.2 | 0.0 | 42.1 |
| | 6 | 88.0 | 89.0 | 40.1 | 0.0 | 0.0 | 38.8 |
| Simetryne* | 4.5 | 96.0 | 97.7 | 14.2 | 0.0 | 0.0 | 0.0 |
| | 6 | 88.0 | 82.1 | 0.0 | 0.0 | 0.0 | 0.0 |
| NTP | 20 | 104.0 | 107.0 | 78.1 | 98.8 | 60.5 | 70.2 |
| | | 96.0 | 90.9 | | | | |
| no weeding | | 100 | 100 | 100 (38.4g /pot) | 100 (4.02g /pot) | 100 (28.4g /pot) | 100 (18.7g /pot) |

Table 2-continued

| Dose of Composition Applied (A.I g/a) | Rice Plant (% to hand weeding weight) | | Weeds (% to no weeding weight) | | | |
|---|---|---|---|---|---|---|
| | Number of tiller | Weight | Barn-yard grass | Eleo-charis acicu-laris | Others Broad-leaved weeds | Others Narrow-leaved weeds |
| hand weeding | 100 (25 tillers /pot) | 100 (20.4g /pot) | — | — | — | — |

Note)
*Simetryne...2-methylthio-4,6-bis(ethylamino)-S-triazine

EXPERIMENTAL EXAMPLE 3

Paddy fields having a variety of naturally occuring weed seeds were plowed and fertilized (with 1 kg of each of N,P$_2$O$_5$ and K$_2$O per a). The paddy fields were then divided into sections each having an area of 10 m$^2$ (2.5 × 4 m.). Stubbles each having two rice seedlings of leaf age 5.0 were replanted in each section with a ridge width of 30 cm and with a stubble width of 15 cm. After the planting, the water depth of the field was maintained at 3 – 5 cm. At leaf ages of 2 – 3 cm of the weeds (15 days after the planting), 300 g/a of NOPA and compounds B, D or H and mixed granules of both compounds were dispersed over the watered paddy field.

The examination of the weed growth was carried out one month after the planting, while the examination of rice yields was carried out after 4 months to give the test results of Table 3.

Table 3

| Dose of Composition Applied (A.I g/a) | | Weeds (% to no weeding (air-dried weight)) | | | | Phytotoxicity Rice Plant | | |
|---|---|---|---|---|---|---|---|---|
| | | Barn-dif-grass | Cyper-us leaf formis | Broad acicu-weeds | Eleo-charis dal laris | Herbici-of phyto-effect | Degree hand-toxicity | Yield (% to weeding) |
| NOPA | 10 | 87.5 | 30.0 | 0.5 | 16.1 | Low | No | 89 |
| | 15 | 85.6 | 18.7 | 0.4 | 12.1 | Low | No | 90 |
| | 20 | 84.7 | 12.7 | 0.1 | 9.8 | Low | No | 91 |
| Compound B | 10 | 0.6 | 0.4 | 37.5 | 11.2 | Moderate | No | 92 |
| | 20 | 0.4 | 0.1 | 29.7 | 2.0 | Moderate | No | 93 |
| Compound D | 10 | 0.2 | 0.7 | 29.6 | 5.7 | Moderate | No | 94 |
| | 20 | 0.1 | 0.2 | 21.4 | 4.1 | Moderate | No | 95 |
| Compound H | 10 | 0.1 | 0.2 | 26.1 | 4.1 | Moderate | No | 91 |
| | 15 | 0 | 0 | 24.5 | 2.5 | High | No | 92 |
| | 20 | 0 | 0 | 16.7 | 1.7 | High | No | 95 |
| Compound J | 10 | 0.7 | 0.8 | 28.7 | 7.8 | Moderate | No | 94 |
| | 15 | 0.2 | 0.4 | 29.6 | 6.2 | Moderate | No | 96 |
| | 20 | 0 | 0 | 18.2 | 2.9 | MOderate | No | 97 |
| Compound M | 10 | 0.6 | 0.7 | 27.4 | 11.4 | Moderate | No | 92 |
| | 15 | 0.1 | 0.4 | 25.6 | 7.1 | Moderate | No | 95 |
| | 20 | 0 | 0 | 18.9 | 2.1 | High | No | 96 |
| Compound O | 10 | 0.9 | 0.8 | 48.6 | 5.7 | Moderate | No | 89 |
| | 15 | 0.7 | 0.3 | 37.2 | 4.5 | Moderate | No | 92 |
| | 20 | 0 | 0 | 29.6 | 1.8 | Moderate | No | 94 |
| NOPA+Compound B | | | | | | | | |
| 10 | 20 | 0.2 | 0.1 | 0.1 | 0.4 | Very High | No | 98 |
| 20 | 20 | 0 | 0.1 | 0 | 0 | Very High | No | 101 |
| NOPA+Compound D | | | | | | | | |
| 10 | 20 | 0.1 | 0.2 | 0 | 0.1 | Very HIgh | No | 96 |
| 20 | 20 | 0 | 0 | 0 | 0 | Very High | No | 99 |
| NOPA+Compound H | | | | | | | | |
| 10 | 10 | 0.3 | 0 | 0 | 0.1 | Very High No | | 98 |
| 10 | 15 | 0.1 | 0.1 | 0 | 0.1 | Very High No | | 97 |
| 10 | 20 | 0 | 0 | 0 | 0 | Very High | No | 101 |
| 15 | 15 | 0 | 0 | 0 | 0 | Very High | No | 104 |
| 15 | 20 | 0 | 0 | 0 | 0 | Very High | No | 102 |
| 15 | 20 | 0 | 0 | 0 | 0 | Very High | No | 101 |
| NOPA+Compound J | | | | | | | | |
| 10 | 10 | 0.1 | 0.1 | 0.2 | 0.1 | Very High | No | 100 |
| 10 | 15 | 0 | 0.2 | 0 | 0 | Very High | No | 104 |
| 10 | 20 | 0 | 0 | 0 | 0 | Very High | No | 102 |
| 15 | 20 | 0 | 0 | 0 | 0 | Very High | No | 107 |
| 20 | 20 | 0 | 0 | 0 | 0 | Very High | No | 102 |
| NOPA+Compound K | | | | | | | | |
| 10 | 10 | 0.2 | 0.3 | 0.1 | 0.1 | Very High | No | 100 |
| 10 | 15 | 0 | 0.1 | 0.2 | 0 | Very High | No | 101 |
| 15 | 20 | 0 | 0 | 0 | 0 | Very High | No | 100 |
| 20 | 20 | 0 | 0 | 0 | 0 | Very High | No | 100 |
| NOPA+Compound N | | | | | | | | |
| 10 | 10 | 0.1 | 0.2 | 0.3 | 0.1 | Very High | No | 102 |
| 10 | 15 | 0 | 0.1 | 0.1 | 0.1 | Very High | No | 104 |
| 15 | 20 | 0 | 0 | 0 | 0 | Very High | No | 102 |
| 20 | 20 | 0 | 0 | 0 | 0 | Very High | No | 101 |
| SWEP.M | 300 | 12.5 | 10.1 | 0.6 | 1.6 | High | Moderate | 91 |
| | | 100 | 100 | 100 | 100 | | | 84 |
| no weeding | | (19.7 g/m$^2$) | 100 | 89.5 g/m$^2$) | (38.4 g/m$^2$) | (6.4 | | 100 |

Table 3-continued

| Dose of Composition Applied yard (A.I g/a) | Weeds (% to no weeding (air-dried weight)) | | | | Phytotoxicity Rice Plant | | |
|---|---|---|---|---|---|---|---|
| | Barn-dif-grass | Cyper-us leaf formis | Broad acicu-weeds | Eleo-charis dal laris | Herbici-of phyto-effect | Degree hand-toxicity | Yield (% to weeding) |
| hand weeding | — | — | — | — | — | — | (84.4 kg/a) |

It is apparent from the above results that the herbicidal composition of the present invention have great weed-controlling effects. The herbicidal composition can easily be obtained as illustrated in detail in the following Examples. All parts appearing in the Examples are parts by weight.

EXAMPLE 1

25 parts of NOPA, 25 parts of Compound A, 45 parts of bentonite and 5 parts of sodium dodecylbenzenesulfonate were mixed to obtain 100 parts of a wettable powder.

EXAMPLE 2

7 parts of NOPA, 7 parts of Compound B, 83 parts of talc, 2 parts of polyoxyethylene glycol monolaurylate and 1 part of naphthalene sulfonate condensate were mixed together and then the resultant mixture was granulated by a conventional method using a granulating machine to obtain 100 parts of a granulate.

EXAMPLE 3

5 parts of NOPA, 7 parts of Compound D, 86 parts of talc and 2 parts of a polyethylene alkylphenyl ether were mixed together and the mixture was granulated by a conventional method using a granulating machine to obtain 100 parts of a granulate.

EXAMPLE 4

20 parts of NOPA, 30 parts of Compound E, 45 parts of talc and 5 parts of naphthalene sulfonate condensate were mixed to obtain 100 parts of a wettable powder.

EXAMPLE 5

30 parts of NOPA, 30 parts of Compound F, 2 parts of sodium ligninsulfonate and 38 parts of talc were mixed to obtain 100 parts of a wettable powder.

EXAMPLE 6

6 parts of NOPA, 7 parts of Compound G, 40 parts of bentonite, 44 parts of talc, 2 parts of sodium ligninsulfonate and 1 part of polyoxyethylenesorbitanalkyl ester were mixed together and the mixture was granulated by a conventional method using a granulating machine to obtain 100 parts of a granulate.

EXAMPLE 7

6 parts of NOPA, 7 parts of Compound H, 84 parts of talc, 2 parts of sodium ligninsulfonate and 1 part of sodium dodecylbenzenesulfonate were mixed together and then the mixture was granulated by a conventional method using a granulating machine to obtain 100 parts of a granulate.

EXAMPLE 8

20 parts of NOPA, 20 parts of Compound J, 4 parts of a sodium alkylbenzenesulfonte and 56 parts of talc were mixed to obtain 100 parts of a wettable powder.

EXAMPLE 9

7 parts of NOPA, 7 parts of Compound K, 40 parts of bentonite, 43 parts of talc, 2 parts of sodium ligninsulfonate and 1 part of polyoxyethylene sorbitanalkyl ester were mixed together and the mixture was granulated by a conventional method using a granulating machine to obtain 100 parts of a granulate.

EXAMPLE 10

7 parts of NOPA, 7 parts of Compound L, 60 parts of bentonite, 2 parts of talc and 4 parts of sodium dodecylbenzenesulfonate were mixed together and the mixture was granulated by a conventional method using a granulating machine to obtain 100 parts of granulate.

EXAMPLE 11

6 parts of NOPA, 7 parts of Compound N, 60 parts of bentonite, 23 parts of talc and 4 parts of sodium N-methyl-N-oleoyl-taurate were mixed together and the mixture was granulated by a conventional method using a granulating machine to obtain 100 parts of granulate.

Although the invention has been described above in preferred Examples, it will be apparent to those skilled in the art that various changes and modifications can be made without departing from the scope of the invention.

What is claimed is:

1. A herbicidal composition for use in paddy fields consisting essentially of a herbicidally effective amount of a mixture of α-(β-naphthoxy)-propionanilide and a synergistic proportion of a compound having the general formula

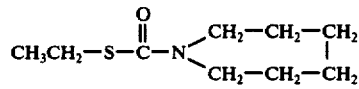

and an inert carrier, the ratio of said α-(β-naphthoxy)-propionanilide to said compound being 1:1-4.

2. A herbicidal composition according to claim 1 wherein said mixture is in the form of granules or a wettable powder.

3. A herbicidal composition according to claim 2 wherein said granules contain therein 1-20% of said mixture.

4. A herbicidal composition according to claim 2, wherein said wettable powder contains therein 10 - 50% of said mixture.

5. A herbicidal composition according to claim 1 further containing an inert diluent, an inert filler or an inert adjuvant.

6. A herbicidal composition according to claim 5, wherein said inert adjuvant is a stabilizing agent, dispersing agent, a suspending agent, a spreader, a penetrating agent or a wet spreader.

* * * * *